US007141078B2

(12) United States Patent
Audousset

(10) Patent No.: US 7,141,078 B2
(45) Date of Patent: *Nov. 28, 2006

(54) OXIDATION DYEING COMPOSITION FOR KERATINOUS FIBER AND DYEING METHOD USING SAME

(75) Inventor: Marie-Pascale Audousset, Asniéres (FR)

(73) Assignee: L'Oreal (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/257,356

(22) PCT Filed: Apr. 11, 2001

(86) PCT No.: PCT/FR01/01108

§ 371 (c)(1),
(2), (4) Date: Nov. 27, 2002

(87) PCT Pub. No.: WO01/78666

PCT Pub. Date: Oct. 25, 2001

(65) Prior Publication Data

US 2003/0233712 A1    Dec. 25, 2003

(30) Foreign Application Priority Data

Apr. 12, 2000    (FR)    .................. 00 04718

(51) Int. Cl.
*A61K 7/13*    (2006.01)
(52) U.S. Cl. ................ 8/405; 8/406; 8/408; 8/409; 8/410; 8/411; 8/421; 8/568; 546/249
(58) Field of Classification Search .......... 8/405, 8/406, 408, 409, 410, 411, 412, 421, 568; 546/249
See application file for complete search history.

(56) References Cited

U.S. PATENT DOCUMENTS

| | | | | |
|---|---|---|---|---|
| 4,003,699 | A | 1/1977 | Rose et al. ............. | 8/102 |
| 4,473,375 | A * | 9/1984 | Clausen ................ | 8/409 |
| 4,754,069 | A | 6/1988 | Braun et al. .......... | 564/440 |
| 4,823,985 | A | 4/1989 | Grollier et al. ........ | 232/1 |
| 4,904,275 | A | 2/1990 | Grollier ................ | 8/408 |
| 5,061,289 | A | 10/1991 | Clausen et al. ........ | 8/405 |
| 5,380,340 | A | 1/1995 | Neunhoeffer et al. .. | 8/409 |
| 5,645,610 | A | 7/1997 | Balzer et al. ......... | 8/411 |
| 5,766,576 | A | 6/1998 | Löwe et al. ........... | 424/62 |
| 5,919,273 | A * | 7/1999 | Rondeau et al. ...... | 8/412 |
| 5,976,195 | A | 11/1999 | de la Mettrie et al. | 8/411 |
| 5,993,490 | A | 11/1999 | Rondeau et al. ...... | 8/409 |
| 6,099,592 | A | 8/2000 | Vidal et al. ........... | 8/409 |
| 6,342,078 | B1 | 1/2002 | de la Mettrie et al. | 8/401 |

FOREIGN PATENT DOCUMENTS

| | | |
|---|---|---|
| DE | 23 59 399 | 6/1975 |
| DE | 31 32 885 A1 | 3/1983 |
| DE | 38 43 892 A1 | 6/1990 |
| DE | 41 33 957 A1 | 4/1993 |
| DE | 195 43 988 A1 | 5/1997 |
| DE | 195 45 854 A1 | 6/1997 |
| DE | 196 10 946 A1 | 9/1997 |
| DE | 198 28 204 C1 | 10/1999 |
| EP | 0 166 155 B1 | 1/1986 |
| EP | 0 687 669 A1 | 12/1995 |
| EP | 0 791 352 | 8/1997 |
| FR | 2 586 913 | 3/1987 |
| FR | 2 733 749 | 11/1996 |
| GB | 1 026 978 | 4/1966 |
| GB | 1 153 196 | 5/1969 |
| JP | 58-34857 A | 3/1983 |
| JP | 61-152620 A | 7/1986 |
| JP | 2-19576 | 1/1990 |
| JP | 5-186319 A | 7/1993 |
| JP | 7-309732 A | 11/1995 |
| JP | 8-3121 A | 1/1996 |
| JP | 9-110659 | 4/1997 |
| JP | 10-218746 A | 8/1998 |
| JP | 2000-86471 A | 3/2000 |
| WO | WO 94/08969 | 4/1994 |
| WO | WO 94/08970 | 4/1994 |
| WO | WO 99/17733 A1 | 4/1999 |

OTHER PUBLICATIONS

Co-pending Application, Composition for the Oxidation Dyeing of Keratin Fibers, Comprising a 3,5-diaminopyridine Derivative and a Particular Thickening Polymer, Marie-Pascale Audousset, filed Oct. 11, 2002.
Co-pending U.S. Appl. No. 10/257,418, Composition for the Oxidation Dyeing of Keratin Fibers, Comprising a 3,5-diaminopyridine Derivative and a Cationic or Amphoteric Polymer, Marie-Pascale Audousset, filed Oct. 11, 2002, Preliminary Amendment Filed: Jan. 10, 2003.

(Continued)

*Primary Examiner*—Eisa Elhilo
(74) *Attorney, Agent, or Firm*—Finnegan, Henderson, Farabow, Garrett and Dunner, L.L.P.

(57) ABSTRACT

The invention concerns an oxidation dyeing composition for keratinous fibers, and in particular human keratinous fibers such as hair, comprising, in a medium suited for dyeing, (a) as first coupling agent at least a 3,5-diamino-pyridine derivative suitably selected; (b) and as second coupling agent at least resorcin (1,3-dihydrobenzene) and/or one of its addition salts with an acid; (c) and as third coupling agent at least an oxidation base such as para-phenylenediamine and/or one of its addition salts with an acid. The invention also concerns the dyeing method using said composition.

29 Claims, No Drawings

OTHER PUBLICATIONS

Co-pending U.S. Appl. No. 10/257,358, Oxidation Dyeing Composition for of Keratinous Fibers and Method Using Same, Marie-Pascale Audousset, filed Oct. 11, 2002, Preliminary Amendment Filed: Nov. 27, 2002.

English language Derwent Abstract of DE 195 45 854, Jun. 12, 1997.

English language Derwent Abstract of DE 196 10 946, Sep. 25, 1997.

English language Derwent Abstract of EP 0 791 352, Aug. 27, 1997.
English language Derwent Abstract of JP 2-19576, Jan. 23, 1990.
English language Derwent Abstract of JP 9-110659, Apr. 28, 1997.
English language Derwent Abstract of DE 198 28 204, Oct. 28, 1999.

English language Patent Abstracts of Japan for JP 5-186319 A.
English language Patent Abstracts of Japan for JP 7-309732 A.
English language Patent Abstracts of Japan for JP 2000-86471 A.

Co-pending U.S. Appl. No. 10/257,355, Oxidation Dyeing Composition for Keratinous Fibres and Method Using Same, Marie-Pascale Audousset, filed Oct. 11, 2002, Preliminary Amendment Filed: Nov. 27, 2002.

Office Action in co-pending U.S. Appl. No. 10/257,355, dated Jan. 12, 2005 (Ex. Elhilo).

Office Action in co-pending U.S. Appl. No. 10/257.358, dated Jan. 12, 2005 (Ex. Elhilo).

Office Action in co-pending U.S. Appl. No. 10/257,418, dated Jul. 14, 2004 (Ex. Ehilo).

Office Action in co-pending U.S. Appl. No. 10/398,423, dated May 12, 2005 (Ex. Elhilo).

* cited by examiner

OXIDATION DYEING COMPOSITION FOR KERATINOUS FIBER AND DYEING METHOD USING SAME

The invention relates to a composition for the oxidation dyeing of keratinous fibers, and in particular of human keratinous fibers such as the hair, comprising, in a medium which is suitable for dyeing,
as a first coupler, at least one suitably chosen 3,5-diaminopyridine derivative;
and, as a second coupler, at least resorcinol (1,3-dihydroxybenzene) and/or one of its addition salts with an acid;
and, as a third coupler, at least one meta-aminophenol and/or one of its addition salts with an acid;
and at least one oxidation base of the para-phenylenediamine type and/or one of its addition salts with an acid.

The invention also relates to the dyeing method using this composition.

The invention also relates to the dyeing method using this composition.

It is known practice to dye keratinous fibers, and in particular human hair, with dye compositions containing oxidation dye precursors, in particular ortho- or para-phenylenediamines, ortho- or para-aminophenols and heterocyclic bases which are generally referred to as oxidation bases. Oxidation dye precursors, or oxidation bases, are colorless or weakly colored compounds which, when combined with oxidizing products, can give rise to colored compounds and dyes by a process of oxidative condensation.

It is also known that the shades obtained with these oxidation bases can be varied by combining them with couplers or color modifiers, the latter being chosen in particular from aromatic meta-diamines, meta-aminophenols, meta-diphenols and certain heterocyclic compounds.

The variety of molecules used as regards the oxidation bases and the couplers allows a wide range of colors to be obtained.

The "permanent" coloration obtained by means of these oxidation dyes must, moreover, satisfy a certain number of requirements. Thus, it must be able to give shades of the desired intensity and it must be able to withstand external agents (light, bad weather, washing, permanent-waving, perspiration, rubbing).

The dyes must also make it possible to cover white hair and, finally, they must be as unselective as possible, i.e. they must give the smallest possible color differences along the same length of keratinous fiber, which may in fact be differently sensitized (i.e. damaged) between its tip and its root.

Oxidation dyeing compositions containing certain 3,5-diaminopyridine derivatives as coupler, in combination with oxidation bases conventionally used in oxidation dyeing, such as, for example, para-phenylenediamines or para-aminophenols, have already been proposed, in particular in patents U.S. Pat. No. 4,473,375 and DE 31 32 885. Such compositions are not, however, always satisfactory, in particular from the point of view of the strengths and the chromaticity of the colorations obtained.

The applicant has now just discovered, completely unexpectedly and surprisingly, that it is possible to obtain novel dyes that are capable of giving strong, particularly chromatic and brilliant, relatively unselective colorations which show excellent properties of resistance to the various attacking factors to which the keratinous fibers may be subjected, by combining a 3,5-diaminopyridine derivative of formula (I) defined below with resorcinol (1,3-dihydroxybenzene) and with a third coupler of the meta-aminophenol type and with at least one oxidation base of the para-phenylenediamine type.

These discoveries form the basis of the present invention.

A first subject of the invention is therefore a composition for the oxidation dyeing of keratinous fibers, and in particular of human keratinous fibers such as the hair, characterized in that it comprises, in a medium which is suitable for dyeing:
as a first coupler, at least one 3,5-diamino-pyridine derivative corresponding to the following general formula (I):

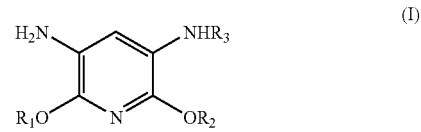

in which:
$R_1$ and $R_2$, which may be identical or different, represent a $C_1$–$C_4$ alkyl radical, a $C_1$–$C_4$ monohydroxyalkyl radical or a $C_2$–$C_4$-polyhydroxyalkyl radical,
$R_3$ represents a hydrogen atom, a $C_1$–$C_4$ alkyl radical, a $C_1$–$C_4$ monohydroxyalkyl radical or a $C_2$–$C_4$ polyhydroxyalkyl radical and/or one of its addition salts with an acid;
and, as a second coupler, at least resorcinol (1,3-dihydroxybenzene) and/or one of its addition salts with an acid;
and, as a third coupler, at least one meta-aminophenol and/or one of its addition salts with an acid;
and at least one oxidation base of the para-phenylenediamine type and/or one of their addition salts with an acid.

The dye composition in accordance with the invention gives strong, very chromatic colorations which show excellent properties of withstanding not only atmospheric agents such as light and bad weather, but also perspiration and the various treatments to which the hair may be subjected.

A subject of the invention is also a method for the oxidation dyeing of keratinous fibers using this dye composition.

Among the 3,5-diaminopyridine derivatives of formula (I) in accordance with the invention, mention may be made of 2,6-dimethoxy-3,5-diaminopyridine, 2,6-diethoxy-3,5-diaminopyridine, 2,6-di-(β-hydroxyethyloxy)-3,5-diaminopyridine and their addition salts with an acid.

According to the invention, the dye composition preferably contains 2,6-dimethoxy-3,5-diaminopyridine and/or at least one of its addition salts with an acid.

The 3,5-diaminopyridine derivative(s) of formula (I) which can be used as a first coupler in the dye composition in accordance with the invention preferably represent(s) from 0.0001 to 10% by weight approximately of the total weight of the dye composition, and even more preferentially from 0.005 to 5% by weight approximately of this weight.

The resorcinol which can be used as a second coupler preferably represents from 0.0001 to 10% by weight approximately of the total weight of the dye composition, and even more preferentially from 0.005 to 5% by weight approximately of this weight.

Among the meta-aminophenols which are used as a coupler in the dye compositions in accordance with the invention, mention may more particularly be made of the following compounds of formula (II) and their addition salts with an acid:

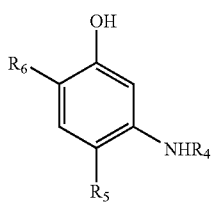

in which:

R₄ represent a hydrogen atom, a $C_1$–$C_4$ alkyl radical, a $C_1$–$C_4$ monohydroxyalkyl radical or a $C_2$–$C_4$ polyhydroxyalkyl radical;

R₅ represents a hydrogen atom, a $C_1$–$C_4$ alkyl radical, a $C_1$–$C_4$ alkoxy radical or a halogen atom chosen from chlorine, bromine or fluorine;

R₆ represents a hydrogen atom, a $C_1$–$C_4$ alkyl radical, a $C_1$–$C_4$ alkoxy radical, a $C_1$–$C_4$ monohydroxyalkyl radical, a $C_2$–$C_4$ polyhydroxyalkyl radical, a $C_1$–$C_4$ monohydroxyalkoxy radical or a $C_2$–$C_4$ polyhydroxyalkoxy radical.

Among the meta-aminophenols of formula (II) above, mention may more particularly be made of meta-aminophenol, 5-amino-2-methoxyphenol, 5-amino-2-(β-hydroxyethyloxy)phenol, 5-amino-2-methylphenol, 5-N-(β-hydroxyethyl)amino-2-methylphenol, 5-N-(β-hydroxyethyl)amino-4-methoxy-2-methylphenol, 5-amino-4-methoxy-2-methylphenol, 5-amino-4-chloro-2-methylphenol, 5-amino-2,4-dimethoxyphenol and 5-(γ-hydroxypropylamino)-2-methylphenol, and their addition salts with an acid.

The meta-aminophenol(s) which can be used as a third coupler preferably represent(s) from 0.0001 to 10% by weight approximately of the total weight of the dye composition, and even more preferentially from 0.005 to 5% by weight approximately of this weight.

Among the para-phenylenediamines which can be used as an oxidation base in the dye composition in accordance with the invention, mention may in particular be made of the following compounds of formula (III) and their addition salts with an acid:

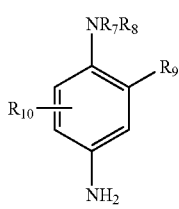

in which:

R₇ represents a hydrogen atom, a $C_1$–$C_4$ alkyl radical, a $C_1$–$C_4$ monohydroxyalkyl radical, a $C_2$–$C_4$ polyhydroxyalkyl radical, a ($C_1$–$C_4$)alkoxy($C_1$–$C_4$)alkyl radical or a $C_1$–$C_4$ alkyl radical substituted with a nitrogenous, phenyl or 4'-aminophenyl group;

R₈ represents a hydrogen atom, a $C_1$–$C_4$ alkyl radical, a $C_1$–$C_4$ monohydroxyalkyl radical, a $C_2$–$C_4$ polyhydroxyalkyl radical, a ($C_1$–$C_4$)alkoxy($C_1$–$C_4$)alkyl radical or a $C_1$–$C_4$ alkyl radical substituted with a nitrogenous group;

R₉ represents a hydrogen atom, a halogen atom such as a chlorine, bromine, iodine or fluorine atom, a $C_1$–$C_4$ alkyl radical, a $C_1$–$C_4$ monohydroxyalkyl radical, a $C_1$–$C_4$ hydroxyalkoxy radical, an acetylamino($C_1$–$C_4$)alkoxy radical, a $C_1$–$C_4$ mesylaminoalkoxy radical or a carbamoylamino($C_1$–$C_4$)alkoxy radical, R₁₀ represents a hydrogen or halogen atom or a $C_1$–$C_4$ alkyl radical.

Among the nitrogenous groups of formula (III) above, mention may in particular be made of amino, mono($C_1$–$C_4$)alkylamino, di($C_1$–$C_4$)alkylamino, tri($C_1$–$C_4$)alkylamino, monohydroxy($C_1$–$C_4$)alkylamino, imidazolinium and ammonium radicals.

Among the para-phenylenediamines of formula (III) above, mention may more particularly be made of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, N-(β-methoxyethyl)-para-phenylenediamine and 2-methyl-1-N-(β-hydroxyethyl)-para-phenylenediamine, and their addition salts with an acid.

Among the para-phenylenediamines of formula (III) above, para-phenylenediamine, para-tolylenediamine, 2-isopropyl-para-phenylenediamine, 2-β-hydroxyethyl-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine and 2-chloro-para-phenylenediamine, and their addition salts with an acid, are most particularly preferred.

The para-phenylenediamines preferably represent from 0.0005 to 12% by weight approximately of the total weight of the dye composition in accordance with the invention, and even more preferentially from 0.005 to 6% by weight approximately of this weight.

The dye composition in accordance with the invention may also contain, in addition to the compound(s) of formula (I) above, to resorcinol and to the meta-aminophenol(s), one or more additional couplers which may be chosen from the couplers conventionally used in oxidation dyeing, and among which mention may in particular be made of substituted meta-diphenols, meta-phenylenediamines and heterocyclic couplers such as, for example, indole derivatives, indoline derivatives, pyridine derivatives other than those of the invention and pyrazolones, and their addition salts with an acid.

These couplers are more particularly chosen from 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-one, 1-phenyl-3-methylpyrazol-5-one and 3-(4-hydroxy-1-methyl-1H-indol-5-ylmethyl)-1-methylpyridinium, and their addition salts with an acid.

When they are present, these additional couplers preferably represent from 0.0001 to 10% by weight approximately of the total weight of the dye composition, and even more preferentially from 0.005 to 5% by weight approximately of this weight.

In addition to the para-phenylenediamines used as oxidation bases, the oxidation dyeing composition in accordance with the invention may contain one or more additional oxidation bases which are preferably chosen from the oxidation bases conventionally used in oxidation dyeing, and among which mention may in particular be made of bisphenylalkylenediamines, para-aminophenols, ortho-aminophenols and heterocyclic bases.

Among the bisphenylalkylenediamines, mention may more particularly be made, by way of example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl) tetramethylenediamine, N,N'-bis(β-hydroxyethyl)-N,N'-bis(4-aminophenyl)-tetramethylenediamine, N,N'-bis(4-methylaminophenyl)-tetramethylenediamine, N,N'-bis (ethyl)-N,N'-bis(4'-amino-3'-methylphenyl)ethylenediamine and 1,8-bis(2,5-diaminophenoxy)-3,5-dioxaoctane, and their addition salts with an acid.

Among the para-aminophenols, mention may more particularly be made, by way of example, of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and their addition salts with an acid.

Among the ortho-aminophenols, mention may more particularly be made, by way of example, of 2-aminophenol, 2-amino-5-methylphenol, 2-amino-6-methylphenol and 5-acetamido-2-aminophenol, and their addition salts with an acid.

Among the heterocyclic bases, mention may more particularly be made, by way of example, of pyridine derivatives, pyrimidine derivatives and pyrazole derivatives.

Among the pyridine derivatives, mention may more particularly be made of the compounds described, for example, in patents GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and their addition salts with an acid.

Among the pyrimidine derivatives, mention may more particularly be made of the compounds described, for example, in German patent DE 2 359 399 or Japanese patent JP 88-169 571 and JP 91-10659 or patent application WO 96/15765, such as 2,4,5,6-tetraamino-pyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine.

Among the pyrazole derivatives, mention may more particularly be made of the compounds described in patents DE 3 843 892 and DE 4 133 957 and patent applications WO 94/08969, WO 94/08970, FR-A-2 733 749 and DE 195 43 988, such as 4,5-diamino-1-methylpyrazole, 3,4-diaminopyrazole, 4,5-diamino-1-(4'-chlorobenzyl)pyrazole, 4,5-diamino-1,3-dimethyl-pyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole and 4,5-diamino-1-β-hydroxyethylpyrazole, and their addition salts with an acid.

The additional oxidation base(s) preferably represent(s) from 0.0005 to 12% by weight approximately of the total weight of the dye composition, and even more preferentially from 0.005 to 6% by weight approximately of this weight.

In general, the addition salts with an acid which can be used in the context of the dye compositions of the invention (pyrazolopyrimidines, compounds of formula (I), additional couplers and oxidation bases) are in particular chosen from hydrochlorides, hydrobromides, sulfates, citrates, succinates, tartrates, lactates and acetates.

The medium which is suitable for dyeing (or support) generally consists of water or of a mixture of water and at least one organic solvent in order to solubilize the compounds which would not be sufficiently water-soluble. By way of organic solvent, mention may be made, for example, of $C_1$–$C_4$ lower alkanols, such as ethanol and isopropanol; glycerol; glycols and glycol ethers such as 2-butoxyethanol, propylene glycol, propylene glycol monomethyl ether, diethylene glycol monoethyl ether and monomethyl ether, and aromatic alcohols such as benzyl alcohol or phenoxyethanol, similar products and mixtures thereof.

The solvents may be present in proportions preferably of between 1 and 40% by weight approximately relative to the total weight of the dye composition, and even more preferentially between 5 and 30% by weight approximately.

The pH of the dye composition in accordance with the invention is generally between 3 and 12 approximately, and preferably between 5 and 11 approximately. It may be adjusted to the desired value by means of acidifying or basifying agents usually used in the dyeing of keratinous fibers.

Among the acidifying agents, mention may be made, by way of example, of inorganic or organic acids such as hydrochloric acid, orthophosphoric acid, sulfuric acid, carboxylic acids such as acetic acid, tartaric acid, citric acid or lactic acid, and sulfonic acids.

Among the basifying agents, mention may be made, by way of example, of aqueous ammonia, alkaline carbonates, alkanolamines such as mono-, di- and triethanolamines, and derivatives thereof, sodium hydroxide, potassium hydroxide and the compounds of formula (IV) below:

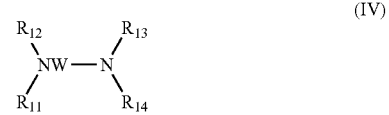

in which W is a propylene residue optionally substituted with a hydroxyl group or a $C_1$–$C_6$ alkyl radical; $R_{11}$, $R_{12}$, $R_{13}$ and $R_{14}$, which may be identical or different, represent a hydrogen atom, a $C_1$–$C_6$ alkyl radical or a $C_1$–$C_6$ hydroxyalkyl radical.

The oxidation dyeing compositions in accordance with the invention may also contain at least one direct dye, in particular to modify the shades or enrich them with glints.

The dye composition in accordance with the invention may also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetrating agents, sequestering agents, fragrances, buffers, dispersing agents, conditioners, such as, for example, volatile or nonvolatile silicones, which are modified or unmodified, film-forming agents, ceramides, preserving agents and opacifiers.

Of course, those skilled in the art will take care to choose this or these optional additional compound(s) such that the advantageous properties intrinsically associated with the oxidation dyeing composition in accordance with the invention are not, or are not substantially, adversely affected by the addition(s) envisioned.

The dye composition according to the invention may be in various forms, such as in the form of liquids, of creams or of gels, or in any other form which is suitable for dyeing keratinous fibers, and in particular human hair.

Another subject of the invention is a method for the oxidation dyeing of keratinous fibers, and in particular human keratinous fibers such as the hair, using the dye composition as defined above.

According to this method, at least one dye composition as defined above is applied to the fibers, the color being developed at acidic, neutral or alkaline pH using an oxidizing agent which is added to the dye composition just at the time of use, or which is present in an oxidizing composition applied simultaneously or sequentially.

According to a preferred embodiment of the dyeing method of the invention, the dye composition described above is preferably mixed, at the time of use, with an oxidizing composition containing, in a medium which is suitable for dyeing, at least one oxidizing agent present in an amount which is sufficient to develop a coloration. The mixture obtained is then applied to the keratinous fibers and is left to stand on them for approximately 3 to 50 minutes, preferably approximately 5 to 30 minutes, after which the fibers are rinsed, washed with shampoo, rinsed again and dried.

The oxidizing agent may be chosen from the oxidizing agents conventionally used for the oxidation dyeing of keratinous fibers, and among which mention may be made of hydrogen peroxide, urea peroxide, alkali metal bromates, persalts such as perborates and persulfates, and enzymes such as peroxidases, laccases, tyrosynases and oxidoreductases, among which mention may in particular be made of pyranose oxidases, glucose oxidases, glycerol oxidases, lactate oxidases, pyruvate oxidases and uricases.

The pH of the oxidizing composition containing the oxidizing agent as defined above is such that, after mixing it with the dye composition, the pH of the resulting composition applied to the keratinous fibers preferably ranges between approximately 3 and 12, and even more preferentially between 5 and 11. It is adjusted to the desired value by means of acidifying or basifying agents usually used in the dyeing of keratinous fibers and as defined above.

The oxidizing composition as defined above may also contain various adjuvants conventionally used in compositions for dyeing the hair and as defined above.

The composition which is finally applied to the keratinous fibers may be in various forms, such as in the form of liquids, of creams or of gels, or in any other form which is suitable for dyeing keratinous fibers, and in particular human hair.

Finally, a subject of the invention is a multicompartment device or dyeing "kit" or any other multicompartment packaging system, a first compartment of which contains the dye composition as defined above and a second compartment of which contains the oxidizing composition as defined above. These devices may be equipped with a means for applying the desired mixture to the hair, such as the devices described in patent FR-2 586 913 in the name of the applicant.

The examples which follow are intended to illustrate the invention without, however, limiting the scope thereof.

| DYEING EXAMPLES | 1 | 2 | 3 |
|---|---|---|---|
| 2,6-Dimethoxy-3,5-diaminopyridine dihydrochloride (coupler of formula (I)) | 0.242 | 0.484 | 0.242 |
| Resorcinol | 0.11 | 0.055 | 0.11 |
| Meta-aminophenol | — | 0.0545 | — |
| 2-Methyl-5-aminophenol (meta-aminophenol coupler) | — | — | 0.369 |
| 2-Methyl-5-N-(2-hydroxyethyl)aminophenol (meta-aminophenol coupler) | 0.668 | — | — |
| Para-phenylenediamine (oxidation base) | — | 0.324 | — |
| N,N-bis-β-hydroxyethyl-para-phenylenediamine sulfate (oxidation base) | 1.872 | — | — |
| 2-Hydroxyethyl-paraphenylenediamine dihydrochloride (oxidation base) | — | — | 1.125 |
| Common dye support No. | 1 | 1 | 2 |
| Demineralized water qs | 100 g | 100 g | 100 g |

Common Dye Support 1

| | |
|---|---|
| Oleyl alcohol polyglycerolated with 2 mol of glycerol | 4 g |
| Oleyl alcohol polyglycerolated with 4 mol of glycerol (78% A.M.) | 5.69 g A.M. |
| Oleic acid | 3.0 g |
| Oleylamine containing 2 mol of ethylene oxide, sold under the trade name Ethomeen O12 by the company Akzo | 7 g |
| Diethylaminopropyl laurylaminosuccinamate, sodium salt containing 55% A.M. | 3 g A.M. |
| Oleyl alcohol | 5 g |
| Oleic acid diethanolamide | 12 g |
| Propylene glycol | 3.5 g |
| Ethyl alcohol | 7.0 g |
| Dipropylene glycol | 0.5 g |
| Propylene glycol monomethyl ether | 9 g |
| Sodium metabisulfite as an aqueous solution containing 35% A.M. | 0.455 g A.M. |
| Ammmonium acetate | 0.8 g |
| Antioxidant, sequestering agent q.s. | |
| Fragrance, preserving agent q.s. | |
| Monoethanolamine q.s. pH 9.8 | |
| Dyes | x g |
| Demineralized water q.s. | 100 g |

Common Dye Support 2

| | |
|---|---|
| Oleyl alcohol polyglycerolated with 2 mol of glycerol | 4 g |
| Oleyl alcohol polyglycerolated with 4 mol of glycerol (78% A.M.) | 5.69 g A.M. |
| Oleic acid | 3.0 g |
| Oleylamine containing 2 mol of ethylene oxide, sold under the trade name Ethomeen O12 by the company Akzo | 7 g |
| Diethylaminopropyl laurylaminosuccinamate, sodium salt containing 55% A.M. | 3 g A.M. |
| Oleyl alcohol | 5 g |
| Oleic acid diethanolamide | 12 g |
| Propylene glycol | 3.5 g |
| Ethyl alcohol | 7.0 g |
| Dipropylene glycol | 0.5 g |
| Propylene glycol monomethyl ether | 9 g |
| Sodium metabisulfite as an aqueous solution containing 35% A.M. | 0.455 g A.M. |
| Ammonium acetate | 0.8 g |
| Antioxidant, sequestering agent q.s. | |
| Fragrance, preserving agent q.s. | |
| Aqueous ammonia containing 20% of $NH_3$ | 10 g |
| Dyes | x g |
| Demineralized water q.s. | 100 g |

METHOD OF APPLICATION

The composition obtained is mixed, weight for weight, with 20 volumes of aqueous hydrogen peroxide, the pH of which is adjusted with a precise amount of 85% pure orthophosphoric acid (2.5 g/100 g of aqueous hydrogen peroxide) for examples 1 and 2, and at pH=3 for example 3. The mixture is applied to permanent-waved grey hair containing 90% of white hairs, in a proportion of 28 g per 3 g of hair, for 30 min. The hair is then rinsed, washed with a standard shampoo and dried.

The results are given in the table below:

| EXAMPLE | SHADE OBTAINED |
|---|---|
| 1 | Purplish blue |
| 2 | Black |
| 3 | Dark gray |

The invention claimed is:

1. A composition for the oxidation dyeing of keratinous fibers comprising, in a medium which is suitable for dyeing:
a first coupler chosen from at least one 3,5-diaminopyridine derivative corresponding to the following general formula (I):

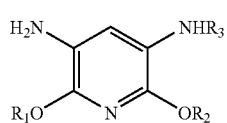

wherein:
$R_1$ and $R_2$, which may be identical or different, are chosen from $C_1$–$C_4$ alkyl radicals, $C_1$–$C_4$ monohydroxyalkyl radicals, and $C_2$–$C_4$-polyhydroxyalkyl radicals;
$R_3$ is chosen from hydrogen, $C_1$–$C_4$ alkyl radicals, $C_1$–$C_4$ monohydroxyalkyl radicals, $C_2$–$C_4$ polyhydroxyalkyl radicals, and one of their addition salts with an acid;
a second coupler chosen from resorcinol and one of its addition salts with an acid;
a third coupler chosen from a meta-aminophenol and one of its addition salts with an acid, wherein the amount of the third coupler ranges from about 0.0001% to about 10% by weight relative to the total weight of the composition; and
at least one oxidation base chosen from bases of the para-phenylenediamine type and one of its addition salts with an acid.

2. The composition of claim 1, wherein the keratinous fibers are human keratinous fibers.

3. The composition of claim 2, wherein the human keratinous fibers are human hair.

4. The composition of claim 1, wherein the at least one 3,5-diaminopyridine derivative of formula (I) is chosen from 2,6-dimethoxy-3,5-diaminopyridine, 2,6-diethoxy-3,5-diaminopyridine, 2,6-di(β-hydroxyethyloxy)-3,5-diaminopyridine, and their addition salts with an acid.

5. The composition of claim 1, wherein the at least one 3,5-diaminopyridine derivative of formula (I) is 2,6-dimethoxy-3,5-diaminopyridine and one of its addition salts with an acid.

6. The composition of claim 1, wherein the amount of the at least one 3,5-diaminopyridine derivative of formula (I) ranges from about 0.0001% to about 10% by weight relative to the total weight of the composition.

7. The composition of claim 1, wherein the amount of the resorcinol and/or one of its addition salts with an acid ranges from about 0.0001% to about 10% by weight relative to the total weight of the composition.

8. The composition of claim 1, wherein the meta-aminophenol corresponds to the following formula (II):

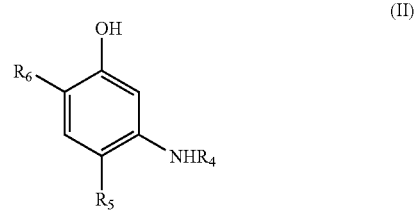

wherein:
$R_4$ is chosen from hydrogen, $C_1$–$C_4$ alkyl radicals, $C_1$–$C_4$ monohydroxyalkyl radicals, and $C_2$–$C_4$ polyhydroxyalkyl radicals;
$R_5$ is chosen from hydrogen, $C_1$–$C_4$ alkyl radicals, $C_1$–$C_4$ alkoxy radicals, and halogens; and
$R_6$ is chosen from hydrogen, $C_1$–$C_4$ alkyl radicals, $C_1$–$C_4$ alkoxy radicals, $C_1$–$C_4$ monohydroxyalkyl radicals, $C_2$–$C_4$ polyhydroxyalkyl radicals, $C_1$–$C_4$ monohydroxyalkoxy radicals, and $C_2$–$C_4$ polyhydroxyalkoxy radicals.

9. The composition of claim 8, wherein the halogens are chosen from chlorine, bromine, and fluorine.

10. The composition of claim 8, wherein the meta-aminophenol of formula (II) is chosen from meta-aminophenol, 5-amino-2-methoxyphenol, 5-amino-2-(β-hydroxyethyloxy)phenol, 5-amino-2-methylphenol, 5-N-(β-hydroxyethyl)amino-2-methylphenol, 5-N-(β-hydroxyethyl)amino-4-methoxy-2-methylphenol, 5-amino- 4-methoxy-2-methylphenol, 5-amino-4-chloro-2-methylphenol, 5-amino-2,4-dimethoxyphenol and 5-(γ-hydroxypropylamino)-2-methylphenol, and their addition salts with an acid.

11. The composition of claim 1, wherein the at least one oxidation base chosen from the para-phenylenediamine type corresponds to the following formula (III):

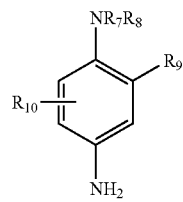

wherein:
R$_7$ is chosen from hydrogen, C$_1$–C$_4$ alkyl radicals, C$_1$–C$_4$ monohydroxyalkyl radicals, C$_2$–C$_4$ polyhydroxyalkyl radicals, (C$_1$–C$_4$)alkoxy(C$_1$–C$_4$)alkyl radicals, and C$_1$–C$_4$ alkyl radical substituted with a group chosen from nitrogenous, phenyl, and 4'-aminophenyl groups;
R$_8$ is chosen from hydrogen, C$_1$–C$_4$ alkyl radicals, C$_1$–C$_4$ monohydroxyalkyl radicals, C$_2$–C$_4$ polyhydroxyalkyl radicals, (C$_1$–C$_4$)alkoxy(C$_1$–C$_4$)alkyl radicals, and C$_1$–C$_4$ alkyl radicals substituted with a nitrogenous group;
R$_9$ is chosen from hydrogen, halogens, C$_1$–C$_4$ alkyl radicals, C$_1$–C$_4$ monohydroxyalkyl radicals, C$_1$–C$_4$ hydroxyalkoxy radicals, acetylamino(C$_1$–C$_4$)alkoxy radicals, C$_1$–C$_4$ mesylaminoalkoxy radicals, and carbamoylamino(C$_1$–C$_4$)alkoxy radicals; and
R$_{10}$ is chosen from hydrogen, halogens, C$_1$–C$_4$ alkyl radicals, and their addition salts with an acid.

12. The composition of claim 11, wherein the halogens are chosen from chlorine, bromine, iodine, and fluorine.

13. The composition of claim 11, wherein the para-phenylenediamine is chosen from para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl) aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, N-(β-methoxyethyl)-para-phenylenediamine, and 2-methyl-1-N-(β-hydroxyethyl)-para-phenylenediamine, and their addition salts with an acid.

14. The composition of claim 1, wherein the amount of the para-phenylenediamine ranges from about 0.0005% to about 12% by weight relative to the total weight of the composition.

15. The composition of claim 1, wherein the composition further comprises one or more additional couplers which are different from said at least one 3,5-diaminopyridine derivative of formula (I), from said resorcinol and from said meta-aminophenol.

16. The composition of claim 15, wherein the additional couplers are chosen from substituted meta-diphenols, meta-phenylenediamines, heterocyclic couplers, and their addition salts with an acid.

17. The composition of claim 15, wherein the amount of the additional couplers ranges from about 0.0001% to about 10% by weight relative to the total weight of the composition.

18. The composition of claim 16, wherein the amount of the additional couplers ranges from about 0.0001% to about 10% by weight relative to the total weight of the composition.

19. The composition of claim 1, wherein the composition further comprises one or more additional oxidation bases other than the para-phenylenediamine type.

20. The composition of claim 19, wherein the additional oxidation bases are chosen from bisphenylalkylenediamines, para-aminophenols, ortho-aminophenols and heterocyclic bases.

21. The composition of claim 19, wherein the amount of the additional oxidation bases ranges from about 0.0005% to about 12% by weight relative to the total weight of the composition.

22. The composition of claim 20, wherein the amount of the additional oxidation bases ranges from about 0.0005% to about 12% by weight of the total weight of the composition.

23. The composition of claim 1, wherein the addition salts with an acid are chosen from hydrochlorides, hydrobromides, sulfates, tartrates, lactates, and acetates.

24. A method for dyeing keratinous fibers comprising applying to the keratinous fibers at least one dye composition for the oxidation dyeing of keratinous fibers comprising, in a medium which is suitable for dyeing:
a first coupler chosen from at least one 3,5-diaminopyridine derivative corresponding to the following general formula (I):

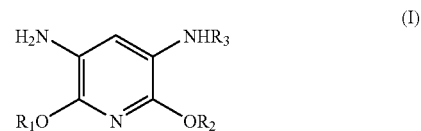

wherein:
R$_1$ and R$_2$, which may be identical or different, are chosen from C$_1$–C$_4$ alkyl radicals, C$_1$–C$_4$ monohydroxyalkyl radicals, and C$_2$–C$_4$-polyhydroxyalkyl radicals,
R$_3$ is chosen from hydrogen, C$_1$–C$_4$ alkyl radicals, C$_1$–C$_4$ monohydroxyalkyl radicals, C$_2$–C$_4$ polyhydroxyalkyl radicals, and one of their addition salts with an acid;
a second coupler chosen from resorcinol and one of its addition salts with an acid;
a third coupler chosen from a meta-aminophenol, and one of its addition salts with an acid, wherein the amount of the third coupler ranges from about 0.0001% to about 10% by weight relative to the total weight of the composition; and
at least one oxidation base chosen from bases of the para-phenylenediamine type, and one of their addition salts with an acid, wherein a color is developed by exposing the dye composition to an acidic, neutral, or alkaline pH using an oxidizing agent that is added to the dye composition at the time of use, or that is present in an oxidizing composition applied to the fibers simultaneously or sequentially.

25. The method of claim 24, wherein the keratinous fibers are human keratinous fibers.

26. The method of claim 25, wherein the human keratinous fibers are human hair.

27. The method of claim 24, wherein the oxidizing agent present in the oxidizing composition is chosen from hydrogen peroxide, urea peroxide, alkali metal bromates, persalts, peracids, and enzymes.

28. The method of claim 27, wherein the persalts are chosen from perborates, percarbonates, and persulfates.

29. A multi-compartment device or multi-compartment dyeing kit comprising:

(1) a first compartment containing a dye composition for the oxidation dyeing of keratinous fibers comprising, in a medium which is suitable for dyeing:

a first coupler chosen from at least one 3,5-diaminopyridine derivative corresponding to the following general formula (I):

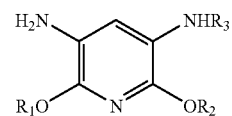

wherein:
$R_1$ and $R_2$, which may be identical or different, are chosen from $C_1$–$C_4$ alkyl radicals, $C_1$–$C_4$ monohydroxyalkyl radicals, and $C_2$–$C_4$-polyhydroxyalkyl radicals;
$R_3$ is chosen from hydrogen, $C_1$–$C_4$ alkyl radicals, $C_1$–$C_4$ monohydroxyalkyl radicals, $C_2$–$C_4$ polyhydroxyalkyl radicals, and one of their addition salts with an acid;
a second coupler chosen from resorcinol and one of its addition salts with an acid;
a third coupler chosen from a meta-aminophenol, and one of its addition salts with an acid, wherein the amount of the third coupler ranges from about 0.0001% to about 10% by weight relative to the total weight of the composition;
at least one oxidation base chosen from oxidation bases of the para-phenylenediamine type and one of its addition salts with an acid; and (2) a second compartment containing an oxidizing composition.

* * * * *